United States Patent
Perret et al.

(10) Patent No.: US 7,232,886 B2
(45) Date of Patent: Jun. 19, 2007

(54) METHOD FOR THE MANUFACTURE OF RECOMBINANT UNHYDROXYLATED COLLAGEN POLYPEPTIDE FIBRES, AND RECOMBINANT UNHYDROXYLATED COLLAGEN POLYPEPTIDE FIBRES OBTAINED THEREBY

(75) Inventors: Stephanie Perret, Saint Georges Encouzan (FR); Florence Ruggiero, Villeurbanne (FR)

(73) Assignee: Meristem Therapeutics, Clermont Ferrand (FR)

( * ) Notice: Subject to any disclaimer, the term of this patent is extended or adjusted under 35 U.S.C. 154(b) by 393 days.

(21) Appl. No.: 10/265,057

(22) Filed: Oct. 4, 2002

(65) Prior Publication Data

US 2003/0129699 A1 Jul. 10, 2003

Related U.S. Application Data

(63) Continuation of application No. PCT/IB01/00569, filed on Apr. 9, 2001.

(30) Foreign Application Priority Data

Apr. 10, 2000 (FR) ................................. 00 04738

(51) Int. Cl.
*C07K 14/78* (2006.01)
*A61F 2/06* (2006.01)
*A61K 38/39* (2006.01)

(52) U.S. Cl. .................... 530/356; 435/69.1; 623/1.47; 623/917

(58) Field of Classification Search ................ 530/356
See application file for complete search history.

(56) References Cited

U.S. PATENT DOCUMENTS

| | | | | |
|---|---|---|---|---|
| 5,733,337 A | * | 3/1998 | Carr et al. | ................. 435/325 |
| 5,856,308 A | * | 1/1999 | St. Pierre et al. | ............. 514/18 |
| 6,428,978 B1 | * | 8/2002 | Olsen et al. | ............... 435/69.1 |
| 6,492,508 B1 | * | 12/2002 | Gruskin et al. | ............ 536/23.5 |
| 6,617,431 B1 | * | 9/2003 | Gruber et al. | .............. 530/356 |
| 2004/0005663 A1 | * | 1/2004 | Bell et al. | .................. 435/69.1 |

OTHER PUBLICATIONS

Stéphanie Perret, Christine Merle, Simonetta Bernocco, Patricia Berland, Robert Garrone, David J. S. Hulmes, Manfred Theisen, and Florence Ruggiero. J. Biol. Chem. 2001. 276: 43693-43698.*

Hélène Chanut-Delalande, Agne's Fichard, Simonetta Bernocco, Robert Garrone, David J. S. Hulmes, and Florence Ruggiero. J. Biol. Chem. 2001. 276: 24352-242359.*

Agnes Fichard, Emmanuelle Tillet, Frederic Delacoux, Robert Garrone, and Florence Ruggiero. J. Biol. Chem. 1997. 272: 30083-30087.*

Noishiki Y, Ma XH, Yamane Y, Satoh S, Okoshi T, Takahashi K, Iwai Y, Kosuge T, Ichikawa Y, Yamazaki I, Mo M. Artif Organs. 1998. 22: 672-680.*

Cloft HJ, Kallmes DF, Lin HB, Li ST, Marx WF, Hudson SB, Helm GA, Lopes MB, McGraw JK, Dion JE, Jensen ME. Radiology. 2000. 214: 557-562.* el-Massry S, Saad E, Sauvage LR, Zammit M, Smith JC, Davis CC, Rittenhouse EA, Fisher LD. J Vasc Surg. 1994. 19: 487-494.*

International Search Report PCT/IB01/00569.

* cited by examiner

*Primary Examiner*—Robert A. Wax
(74) *Attorney, Agent, or Firm*—Edwards Angell Palmer & Dodge

(57) ABSTRACT

The present invention relates to a process for the production of fibres of an unhydroxylated recombinant collagen polypeptide, and the fibres obtained thereby, as well as to uses of such fibres as a biomaterial.

27 Claims, 2 Drawing Sheets

METHOD FOR THE MANUFACTURE OF RECOMBINANT UNHYDROXYLATED COLLAGEN POLYPEPTIDE FIBRES, AND RECOMBINANT UNHYDROXYLATED COLLAGEN POLYPEPTIDE FIBRES OBTAINED THEREBY

This application claims priority under 35 U.S.C. §120 to International Application PCT/IB01/00569, filed Apr. 9, 2001 which claims priority to FR 00/04738, filed Apr. 10, 2000.

The present invention relates to a method for the manufacture of recombinant collagen polypeptide fibres, and more particularly to recombinant unhydroxylated collagen polypeptide fibres.

Collagen polypeptides make up a large family of structural polymers based on polypeptide chains assembled into helices, either as heterotrimers, or as homotrimers, and which are present or produced in an important number of cells, for example animal, mammalian, human, fish or jellyfish. At present, approximately twenty types of human collagen have been identified, each one playing a particular role in the human body.

Generally, methods for manufacturing native collagen fibres, for example from bovine sources are well known. It is for example, known, that in animal tissues, type I collagen is present as fibres in the extracellular matrix, and that theses fibres can easily be made to reform after extraction of the native collagen in appropriate conditions. As an example, the classical method for forming fibres in the laboratory from native collagen in solution is to place the native collagen in a saline phosphate buffer at pH 7 (PBS) at 4° C., and then to raise the temperature to 35° C. The native collagen then polymerises into striated fibres that can be accumulated into a pellet by centrifugation.

The stability of the helices, and even the collagen polypeptide fibres themselves, has traditionally been characterized and identified as being related to the high degree of hydroxylation of the molecules, mainly at the hydroxyproline amino acid residues, which is present in relatively important amounts in the polypeptide chain. Insofar as recombinant collagen is concerned, the collagen polypeptide that is formed is only hydroxylated if its production occurs in a cell producing native collagen, since in this case the cell also produces a biosynthetic enzyme that is essential to hydroxylation, that is prolyl-4-hydroxylase. It has been demonstrated that certain recombinant cells, or those that have been genetically modified, and did not normally contain any genes coding for the production of a native collagen, could not form stable hydroxylated collagen polypeptides at physiological temperatures (Berg, R. A et Prockrop, D. J, 1973) without this enzyme, which is responsible for post-translational hydroxylation of the prolines situated in the Y amino acid position of the collagen chain Gly-X-Y triplet. Attempts have been reported, while expressing collagen alpha I or alpha II chains in Pichia or baculovirus cells, to co-express a gene coding for prolyl-4-hydroxylase, in order to ascertain whether a homotrimeric recombinant and hydroxylated collagen could be produced.

One might note that all previous attempts have thus focussed on making the recombinant collagen peptide as conform as possible to the native equivalent, since it was believed that recombinant unhydroxylated collagen polypeptides could not form or be made to form fibres in a stable manner, which in turn would have enabled them to be transformed and be used as biomaterials in much the same way as native collagen.

The applicant of the present invention has however managed to avoid the time-consuming and delicate approach involving co-expression of hydroxylating enzymes, and against all received wisdom in the field of recombinant collagen production has managed to produce recombinant unhydroxylated collagen polypeptide fibres, via a specific method of production. The fibres obtained by this method can thereafter be transformed according to various processes, in order to obtain products that may be used as biomaterials similar to those found for native collagen. An object of the present invention is therefore a method for the production of unhydroxylated recombinant collagen polypeptide fibres, characterised in that fibrillogenesis is carried out under the following conditions:

a temperature comprised between about 4° C. and about 26° C.;

the unhydroxylated recombinant collagen polypeptide is diluted in an acid;

the unhydroxylated recombinant collagen polypeptide is dialysed at a temperature lower than the usual physiological temperature of corresponding native collagen.

Furthermore, another object of the present invention is unhydroxylated recombinant collagen polypeptide fibres, obtained by the process of the preceding method.

Preferably, the unhydroxylated recombinant collagen polypeptide is of plant origin. Other unhydroxylated recombinant collagen polypeptides can also be used in the method of the present invention. These recombinant polypeptides can be, for example, produced by cells that do not normally produce hydroxylated collagen, for example unhydroxylated recombinant collagen polypeptides produced by yeasts, such as *Pichia* sp., or more preferably *Pichia pastoris*, or even *Saccharomyces* sp., such as *Saccharomyces cerevisiae*, or even insect cells, such as those from baculovirus, or even bacterial cells such as *Escherichia coli* and the like.

Preferably, the unhydroxylated recombinant collagen polypeptide of plant origin is obtained by insertion of one or more DNA sequences coding for said polypeptide into a plant, or else into a cell that does not normally produce collagen.

The unhydroxylated recombinant collagen polypeptides used in the method according to the present invention generally comprise several chains, for example alpha chains of human collagen. These chains can be of different types, depending on the recombinant collagen polypeptide that it is desired to use. In a preferred embodiment of the present invention, the recombinant collagen polypeptide is a collagen comprising at least one alpha I human chain. In a more preferred embodiment, the recombinant collagen polypeptide is a collagen comprising at least one alpha I human chain, and at least one other alpha human chain. Even more preferably, the recombinant collagen polypeptide is a collagen comprising at least three alpha I human chains.

According to a particularly preferred embodiment of the present invention, the polypeptide is diluted in an acid at a concentration of about 200 mg/ml.

Even more preferably, the acid is 0.1M acetic acid.

In another preferred embodiment of the present invention, a dialysis is carried out at 4° C.

Even more preferably, the dialysis is carried out against a monopotassium phosphate buffer without the addition of salts.

In a particularly preferred embodiment of the present invention, the dialysis is carried out against a 10 mM pH 7 monopotassium phosphate buffer for 12 hours.

Another object of the present invention are fibres of unhydroxylated recombinant collagen polypeptide obtainable by fibrillogenesis carried out under the following conditions:
- a temperature comprised between about 4° C. and about 26° C.;
- the unhydroxylated recombinant collagen polypeptide is diluted in an acid;
- the diluted unhydroxylated recombinant collagen polypeptide dilué is dialysed below the usual physiological temperature of the corresponding native collagen.

Preferably, the fibres can be obtained according to previously described preferred embodiments. Advantageously, and preferably, the fibres formed after dialysis are separated by centrifugation.

According to a more preferred embodiment of the previous embodiment, centrifugation can be carried out at 20000 G for 10 minutes.

In accordance with a particularly preferred embodiment of the present invention, the unhydroxylated recombinant collagen polypeptide fibres have a diameter comprised between about 100 nm and about 200 nm.

Still further objects of the present invention are biomaterials obtained from, or based on, the fibres manufactured according to the present invention, which fibres may be preferably reticulated. In one preferred embodiment of the invention, the biomaterial is in the form of a sponge.

According to another preferred embodiment, the biomaterial is in the form of a film or a gel. Preferably, and depending on the intended application, this film or gel may or may not adhere to human tissues.

In an even more preferred embodiment, the biomaterial has a three dimensional structure, preferably in the form of a tube. According to a preferred embodiment, the biomaterial based on, or obtained from unhydroxylated recombinant collagen polypeptide fibres is associated, by gluing, spraying, induction, impregnation, fusion or extrusion to or into a prosthetic structure. Such structures are known generally in the prior art, since collagen is often used to cover such prosthetic structures, for example in order to avoid post-operative adhesions, or to insure leaktightness of the structure with respect to the flow of corporeal liquids, such as in the vascular circulatory system. Therefore, and in a preferred embodiment, the prosthetic structure is a knitted or unknitted web, or a vascular prosthesis, and even more preferably is an endovascular prosthesis, such as a stent. The present invention will be better understood by the following detailed description of one or more preferred embodiments, starting from an unhydroxylated recombinant collagen polypeptide obtained from a recombinant or transgenic plant cell. The detailed description that follows is given purely as a non-limiting illustration of the different objects that comprise the present invention.

In another embodiment of the present invention, unhydroxylated recombinant collagen polypeptide fibres can be obtained via an alternative method that does not use dialysis, under the following conditions:
- diluting unhydroxylated recombinant collagen polypeptide in acid;
- contacting the unhydroxylated recombinant collagen solution with a buffer at high pH, wherein the resulting final solution has neutral pH and a concentration of unhydroxylated recombinant collagen lower than that of the initial concentration.

Preferably, the method is carried out below the denaturation temperature of the equivalent native collagen polypeptide, and more preferably from 4° C. to 26° C., even more preferably at about 10° C.

According to a more preferred embodiment of this method, the unhydroxylated recombinant collagen polypeptide is diluted in an organic acid, and preferably in acetic acid. Preferably, the unhydroxylated recombinant collagen polypeptide is diluted in the acid at an initial concentration of 400 mg/ml.

According to this preferred embodiment of the invention, the solution of unhydroxylated recombinant collagen polypeptide is contacted with a buffer at high pH. Preferably, the buffer is a phosphate buffer, for example monopotassium phosphate buffer, and is most preferably concentrated, for example twice concentrated. The pH of the buffer is high, and preferably between 11 and 14, more preferably about 12, and most preferably 12.3. In a most preferred embodiment, one volume of buffer is contacted with one volume equivalent of unhydroxylated recombinant collagen polypeptide in acid, and the final concentration after neutralisation is 200 mg/ml of unhydroxylated recombinant collagen polypeptide.

EXAMPLE

Figure 1:
FIG. 1 represents the image obtained from a transmission electron microscope of the unhydroxylated recombinant collagen type I polypeptide fibres formed after applying the method according to the present invention.

A recombinant collagen polypeptide is extracted from stably transformed tobacco plants containing a cDNA coding for a N-propeptide deleted alpha 1(I) human collagen chain. The collagen polypeptide is purified and present after purification as a $[?1(I)]_3$ triple helice in which the C-propeptide domain is cleaved in planta. The recombinant collagen polypeptide is soluble in 0.1M acetic acid. An amino acid analysis of the thus obtained polypeptide demonstrated that it was not hydroxylated at the proline residues, leading to a lowering of its denaturation temperature down to 30° C. instead of 41.5° C. for a control bovine collagen sample.

In tissues, native type I collagen is present as fibres in the extracellular matrix.

When fibrillogenesis is carried out in vitro, observation under the electron microscope enables evaluation of the presence or absence of formation of fibres.

In vitro fibrillogenesis of the unhydroxylated recombinant collagen polypeptide was compared with that of bovine homotrimeric $[a1(I)]_3$ collagen. Multiple experiments were carried out in which buffer, temperature, and ionic strength were tested. The usual conditions for fibrillogenesis had to be modified for the recombinant collagen polypeptide of plant origin, which is not hydroxylated and has a denaturation temperature of 30° C. Temperatures exceeding 28 to 30° C. were thus excluded and those varying from 4° C. to 26° C. were selected. Phosphate buffers in the presence of salts (PBS, 20 mM monopotassium phosphate with or without added 140 mM de sels), pH variation from neutral to basic, and finally collagen polypeptide concentration variation in solution (200 mg à 2 mg/ml) did not permit the formation of fibres with the unhydroxylated recombinant collagen polypeptide, as opposed to bovine homotrimeric collagen, under which conditions only a network of fine fibrils were obtained. In the end, only a single set of conditions was demonstrated to be effective in forming fibres for the unhydroxylated recombinant collagen polypeptide obtained from transformed plants.

The unhydroxylated recombinant collagen polypeptide was diluted to 200 mg/ml in 0.1 M acetic acid, then dialysed at 4° C. against a 10 mM pH 7 monopotassium phosphate buffer for 12 heures. After centrifugation at 20000 G for 10 minutes, the fibres that had formed were collected in the pellet, as opposed to the molecules still in solution. The pellet obtained was resuspended in a volume of dialysis buffer five times less than that of the volume of the supernatant. A fraction of the supernatant and the pellet was deposited on a 6% acrylamide SDS-PAGE electrophoresis gel. The gel showed that the recombinant collagen polypeptide, as with the native bovine homotrimeric control collagen, was present majoritarily in the pellet. After negative staining, the collagen polypeptide contained in the pellet was observed under a transmission electronic microscope. With the recombinant collagen polypeptide, the presence of fibres was observed in diameters ranging from about 100 to about 200 nm. The native bovine homotrimeric collagen under these conditions had polymerised into fibrils ranging from 10 to 40 nm in diameter, and these fibrils were not striated, even though native collagen is capable of doing so under other conditions of higher ionic strength.

The fibres formed from unhydroxylated recombinant collagen polypeptide were obtained, according to one preferred embodiment of the present invention, in a phosphate buffer without the addition of salts, whereas the presence of such salts is important for obtaining striated fibres in vitro from native collagens. In the conditions described above, and without wishing to be limited by any theory, it appears that the absence of salts results in an increase in electrostatic interactions and thus enables precipitation of the unhydroxylated recombinant collagen polypeptide as striated fibres.

Collagen Stability

It is likely that the unhydroxylated recombinant collagen polypeptide is stabilized through its fibrillar structure. The stability was tested by digestion with trypsin at varying temperatures. After a twenty minute incubation at a given temperature, the unhydroxylated recombinant collagen polypeptide was contacted with trypsin. The persistence of a migrating band using gel electrophoresis corresponding to that of an intact alpha 1(I) chain was used to determine the resistance, and thereby the absence or presence of denaturation of the unhydroxylated recombinant collagen polypeptide. The stability of the collagen polypeptide at 37° C. was also tested over time.

Reticulation

In order to improve the stability of the unhydroxylated recombinant collagen polypeptide, the latter was reticulated in the form of fibres and the denaturation temperature tested again. In order to do this, several different reticulating agents of varying sizes (7.7A, 11.4A, etc.) were tested, for example disuccinimide glutarate (DSG), which is a homobifunctional molecule of 7.7A. These agents react with free amines, particularly lysines and the N-terminal extremity of proteins. The collagen polypeptide solution to be reticulated was placed in a solution of 0.01M acetic acid at a concentration less than or equal to 250 mg/ml. This solution was diluted twice in PBS buffer solution that had been concentrated twice. The pH was then adjusted to neutralisation of the solution. Next, a solution of reticulating agent was prepared at a concentration of 5 mM. One volume of this solution was added to the recombinant collagen polypeptide solution at a molar concentration fifty times that of the collagen. The mixture was incubated at 4° C. for 5 to 20 minutes. The reaction was stopped by the addition of a final 0.1M tris solution. The reticulation of the collagen polypeptide was controlled by gel electrophoresis with an acrylamide gradient of 3.5 to 5%. The conversion of the migrating band corresponding to the alpha 1 collagen chain into a band migrating at a size of 300 kDa demonstrated reticulation of the collagen.

Gel Formation

The formation of a dense gel can be carried out rapidly by instantly changing pH, ionic strength and temperature. In order to do this, a solution of collagen polypeptide at 1.5 to 3 mg/ml concentration in acetic acid was mixed (1:1 vol/vol) with serum-free culture media that had been concentrated twice. The pH was rapidly adjusted to neutralisation with sodium hydroxide. The mixture was incubated at different temperatures, and the conditions for pH or ionic strength were also modified in order to improve formation of the gel. The gel thus obtained was prepared for examination under the transmission electron microscope.

Study of the Fibres

Figure 2:
FIG. 2 represents the image obtained from a transmission electron microscope of native collage type I fibres obtained through traditional fibrillogenesis.

The fibres formed from unhydroxylated recombinant collagen in a 10 mM pH 7 phosphate buffer via dialysis at 4° C. were analysed after positive staining with uranium acetate and tungsten phosphoric acid under a transmission electron microscope. Both striated and non-striated fibres were observed as is clear from FIG. 1. FIG. 1 is a representation of the image obtained from the transmission electron microscope of the unhydroxylated collagen type I polypeptide fibres formed after applying the method according to the present invention. The striated fibres had a periodicity of approximately 67 nanometers along the axis of the fibre, which is characteristic of the periodicity observed in native collagen I fibres. FIG. 2 represents the image obtained from the transmission electron microscope of native collage type I fibres obtained through traditional fibrillogenesis. The diameter of the unhydroxylated recombinant collagen fibres obtained and illustrated in FIG. 1 varied from about 30 to about 550 nanometers, the average diameter being about 156 nanometers.

The kinetics of fibre formation were determined by turbidimetry at 315 nanometers. Quartz cells were placed in a spectrophotometer equipped with a water cooling system at 10° C. One volume of 10 mM 2× concentrated phosphate buffer, the pH of which was adjusted to 12.3 and one equivalent volume of a solution of 10 mM acetic acid containing 400 mg/ml of collagen, were successively added to the cell, in order to obtain a neutral pH and a final concentration of 200 mg/ml. As soon as the collagen was added to the cell, a rapid increase in the turbidity was noted. This first observation followed by a progressive increase in turbidity until a plateau was reached. The curve obtained was in conformity with those observed in fibrillogenesis experiments with native collagen I. Observation of the fibres under a transmission electron microscope after staining at the end of the kinetics measurements showed the presence of striated fibres. It was therefore possible to obtain fibres' of unhydroxylated recombinant collagen polypeptide using this method as an alternative to dialysis.

Denaturation Temperature

The denaturation temperature of the unhydroxylated recombinant collagen in fibrous form was determined by circular dichroism. The spectra were measured at 10° C. using a CD6 Jobin Yvon spectropolarimeter equipped with a temperature regulation unit. The denaturation temperature of the fibres was measured in 10 mM, pH 7 phosphate buffer at a concentration of 700 µg/ml. The kinetics of denaturation were measured at 230 nm, which corresponds to the maximum signal observed in the spectra prior to denaturation. Temperature was increased in increments of 1° C. every 5 minutes in order to permit temperature stabilization in the measuring chamber. The molecular unhydroxylated recombinant collagen displayed a denaturation temperature of 30° C. (Ruggiero et al, 2000), whereas it increased to 36° C. for the same recombinant collagen in fibrous form. These results indicated that the denaturation temperature of unhydroxylated recombinant collagen had increased by 6° C. when in fibrous form. Such temperature stability enables reticulation to be carried out to further increase the temperature resistance of the molecules and to confer further advantageous mechanical properties to the fibres, such as compression resistance, and tear resistance.

Platelet Adhesion and Aggregation

In general, two different mechanisms can be distinguished in the interaction of platelets with collagen: these mechanisms are known as adhesion and aggregation. The adhesion step occurs within the first moments of contact of the platelet with collagen, but does not necessarily induce aggregation. The latter in vivo leads to the formation of a hemostatic plug upon trauma or injury.

The test for platelet adhesion is a colorimetric test as described by Bellavite et al, 1994. Blood from a healthy volunteer donor was centrifuged for 12 minutes at 200 g and the supernatant corresponding to the platelet rich plasma (PRP) fraction collected. The platelets were subsequently washed to eliminate plasmatic proteins, and then an anticoagulant, for example comprising citric acid, citrate and dextrose (CACD), was added to the platelet rich plasma in a ratio of 1 volume of CACD for 10 volumes of PRP, and 1 µl/ml of $PGE_1$ (prostaglandin E1 stock solution at 100 µg/ml) was also added to inhibit aggregation, and the mixture centrifuged for 7 minutes at 2600 g. The supernatant was eliminated and the platelets resuspended in Jarmieson's buffer (5.5 mM dextrose, 128 mM NaCl, 4.26 mM $Na_2HPO_4$, 7.46 mM $NaH_2PO_4$, 4.77 mM tri Na citrate $2H_2O$, 2.35 mM citric acid [$H_2O$], 0.35% BSA, and 1 µl/ml of $PGE_1$, adjusted to the initial volume of PRP. The suspension was centrifuged again for 7 minutes at 800 g, and the pellet taken up in adhesion buffer, for example comprised of TBS, 5 mM glucose, 0.5% BSA, pH 7.4). The quantity of platelets was adjusted to approximately $10^8$ platelets/millilitre in the adhesion buffer and incubated for at least 30 minutes at ambient temperature. Five minutes before use, 2 mM of $Mg^{2+}$ ions were added to the suspension.

For the adhesion test, 100 microlitres of recombinant collagen fibres, at a concentration of 50 µg/ml in 10 mM pH7 phosphate buffer, were adsorbed onto the wells, of an Immulon 2 plate comprising 96 wells, for 60 minutes at ambient temperature. Each experiment was carried out in triplicate. The wells were subsequently saturated with 50 mg/ml of bovine serum albumin (BSA) in TBS for 30 minutes then washed three times with 100 µl of adhesion buffer. 50 microlitres of platelet suspension were added to each well, and then the plate was incubated for 60 minutes at ambient temperature. The non attached platelets were then eliminated, and the wells washed three times with 200 µl of adhesion buffer. 150 microlitres of lysis buffer (0.1M citrate, pH5.4, 0.1% tritonX100, 5 mM p-nitrophenylphosphate (1.31 mg/ml) were added to each well and left for 60 minutes. The reaction was terminated by the addition of 100 µl of 2M NaOH and the plaque read at 405 nm.

The results indicated that the unhydroxylated recombinant collagen adsorbed at a concentration of 100 µg/ml in fibrous form does show significant adhesion to the platelets when compared to control fibres formed from homotrimeric type I bovine collagen. It appeared from these results that the platelets were not capable of recognizing the unhydroxylated recombinant collagen and thus did not adhere to the latter. This property is useful for example in materials where adhesion is not required or is considered to be a disadvantage or incurs nefarious side-effects, for example in abdominal surgery, where separation of the tissues following placement of prostheses, in particular hernial prostheses is desired. The property can therefore be put to use to form biomaterials, in particular prostheses, such as hernial prostheses, or any other prosthetic device that could be formed from, based on, or coated with such a collagenic material.

The aggregative properties of the unhydroxylated recombinant collagenic polypeptides in fibrous form was also studied. The study was carried out using an aggregometer at a regulated temperature of 20° C., and with PRP obtained as described previously. A control plasma fraction known as Platelet Poor Plasma (PPP) was also used and corresponds to the supernatant obtained by centrifuging PRP for 5 minutes at 8000 g. After addition of the sample, at a concentration comprised between about 50 to about 100 µg/ml, to 400 pl of PRP, the aggregation test was carried out for 12 minutes with magnetic stirring at 900 rpm. The results show that the addition of unhydroxylated recombinant collagen in fibrous form, at the concentrations specified above, does not induce aggregation after 12 minutes. In opposition to these findings, a concentration of 50 µg/ml of heterotrimeric bovine collagen I fibres is capable of inducing platelet aggregation in a few minutes. These results indicate that the unhydroxylated recombinant collagen is not capable of inducing platelet aggregation. Without wishing to be bound by theory, it is thought that these results may probably be explained by the absence of GPO sequences that are normally specifically recognized by the GPVI receptor expressed by the platelets, and which are responsible for platelet aggregation, as described in Knight et al, 1999. These observations have important consequences for the unhydroxylated recombinant collagen fibres of the present invention in that it is possible to use the fibres to form biomaterials that will avoid the problems of aggregation that are well documented with other collagen based or coated products, such as endoprostheses, or other intracorporeal implants. Consequently, devices made from or containing the collagenic polypeptide fibres of the present invention can significantly reduce or even obviate the need for the use of anticoagulants in association with such prosthetics.

The invention claimed is:

1. A method for producing an unhydroxylated recombinant collagen polypeptide fiber comprising:
   a. diluting an unhydroxylated recombinant collagen polypeptide in an acid at a temperature of between about 4° C. and about 26° C.; and
   b. dialyzing the diluted unhydroxylated recombinant collagen polypeptide against a buffer below the usual physiological temperature of the corresponding native collagen to form an unhydroxylated recombinant collagen polypeptide fiber.

2. The method of claim 1, wherein the unhydroxylated recombinant collagen polypeptide is expressed by a plant.

3. The method of claim 1, wherein the unhydroxylated recombinant collagen polypeptide expressed by a plant is obtained by insertion of one or more DNA sequences coding for said polypeptide into a plant.

4. The method of claim 1, wherein the recombinant collagen polypeptide is a collagen comprising at least one human alpha I chain.

5. The method of claim 4, wherein the unhydroxylated recombinant collagen polypeptide is a collagen comprising at least one human alpha I chain, and at least another human alpha chain.

6. The method of claim 4, wherein the unhydroxylated recombinant collagen polypeptide is a collagen comprising at least three human alpha I chains.

7. The method of claim 1, wherein the acid is 0.1M acetic acid.

8. The method of claim 1, wherein the dialysis is carried out at 4° C.

9. The method of claim 1, wherein the dialysis is carried out against a monopotassium phosphate buffer without the addition of salts.

10. The method of claim 9, wherein the dialysis is carried out against a 10 mM pH 7 monopotassium phosphate buffer for 12 hours.

11. The method of claim 1, wherein the fibers formed after dialysis are separated by centrifugation.

12. The method of claim 11, wherein centrifugation is carried out at about 20000 G for about 10 minutes.

13. The method of claim 1, wherein the fibers have a diameter of between about 30 nm to about 550 nm.

14. The method of claim 1, further comprising the step of reticulating said unhydroxylated recombinant collagen fiber.

15. The method of claim 1, further comprising the step of incorporating said unhydroxylated recombinant collagen fiber into a biomaterial.

16. The method of claim 15, wherein said biomaterial is in the form of a sponge.

17. The method of claim 15, wherein said biomaterial is in the form of a film or a gel.

18. The method of claim 17, wherein said film or gel adheres to human tissue.

19. The method of claim 17, wherein said film or gel does not adhere to human tissue.

20. The method of claim 15, wherein said biomaterial has a three dimensional structure.

21. The method of claim 20, wherein said three dimensional structure is the form of a tube.

22. The method of claim 15, wherein said biomaterial is incorporated by gluing, spraying, induction, impregnation, fusion or extrusion to a prosthetic structure.

23. The method of claim 21, wherein said prosthetic structure is a knitted web.

24. The method of claim 23, wherein said prosthetic structure is an unknitted web.

25. The method of claim 21, wherein said prosthetic structure is a vascular prosthesis.

26. The method of claim 23, wherein said prosthetic structure is an endovascular prosthesis.

27. The method of claim 26, wherein said endovascular prosthesis is a stent.

* * * * *